United States Patent [19]

Sirrenberg et al.

[11] Patent Number: 4,764,524
[45] Date of Patent: Aug. 16, 1988

[54] NOVEL SUBSTITUTED FURAZANE

[75] Inventors: Wilhelm Sirrenberg, Sprockhoevel; Rudolph Braden, Odenthal; Heinz Ziemann, Leichlingen; Gerhard Zoebelein, Leverkusen; Wolfgang Pflüger, Leichlingen, all of Fed. Rep. of Germany

[73] Assignee: Bayer Aktiengesellschaft, Leverkusen, Fed. Rep. of Germany

[21] Appl. No.: 816,933

[22] Filed: Jan. 8, 1986

[30] Foreign Application Priority Data

Jan. 19, 1985 [DE] Fed. Rep. of Germany ....... 3501723

[51] Int. Cl.$^4$ .................... C07D 271/08; A01N 47/36
[52] U.S. Cl. .................................... 514/364; 548/125
[58] Field of Search .................... 548/125; 514/364

[56] References Cited

U.S. PATENT DOCUMENTS 4,449,998  5/1984  Lavanish et al. ................. 71/92
4,699,916  10/1987  Sirrenberg ...................... 514/364

FOREIGN PATENT DOCUMENTS 2881     7/1979  European Pat. Off. ............ 548/125
132680   2/1985  European Pat. Off. ............ 548/125
2436179  6/1975  Fed. Rep. of Germany ......... 71/92
3326509  1/1985  Fed. Rep. of Germany ......... 548/125

OTHER PUBLICATIONS

Chemical Abstracts, vol. 79, No. 17, 29 Oct. 1973; Abstract No. 105152k, p. 420.
Chemical Abstracts, vol. 94, No. 5, 2 Feb. 1981, p. 119, Abstract No. 2563r.

Primary Examiner—Robert Gerstl
Attorney, Agent, or Firm—Sprung Horn Kramer & Woods

[57] ABSTRACT

Insecticidally and acaricidally active novel substituted furazanes of the formula

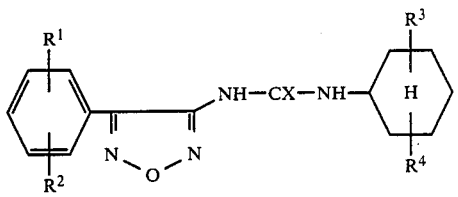

in which
$R^1$ and $R^2$ each independently is hydrogen, halogen, alkyl, alkoxy, alkylthio, halogenoalkyl, halogenoalkoxy, halogenoalkylthio or optionally substituted aryloxy, or
$R^1$ and $R^2$ together are an optionally substituted alkylene radical which is interrupted by 1 or 2 oxygen atoms,
$R^3$ and $R^4$ each independently is hydrogen, alkyl, alkoxy, halogenoalkyl or halogenoalkoxy, and
X is oxygen or sulphur.

11 Claims, No Drawings

NOVEL SUBSTITUTED FURAZANE

The invention relates to new substituted furazanes, processes for their preparation and their use as agents for combating pests, in particular as insecticides and acaricides.

It was not hitherto known that substituted furazanes can be used as agents for combating pests, and it was merely known hitherto that certain heterocyclic compounds, such as, for example, 3-phenyl-2-phenylimino-4,5-bis-(trifluoromethylimino-thiazolidine, have insecticidal properties (compare, for example DE-AS (German Published Specification) No. 2,062,348).

The new substituted furazanes of the formula (I)

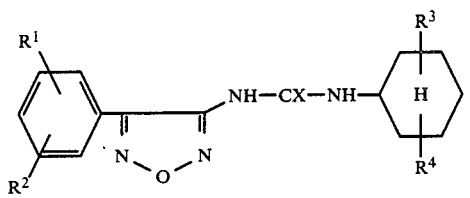

in which
- $R^1$ and $R^2$ are identical or different and represent hydrogen, halogen, alkyl, alkoxy, alkylthio, halogenoalkyl, halogenoalkoxy, halogenoalkylthio or optionally substituted aryloxy, or
- $R^1$ and $R^2$ together represent an optionally substituted alkylene radical, which is interrupted by 1 or 2 oxygen atoms,
- $R^3$ and $R^4$ are identical or different and represent hydrogen, alkyl, alkoxy, halogenoalkyl or halogenoalkoxy and
- X represents oxygen or sulphur, have been found.

It has furthermore been found that the new substituted furazanes of the formula (I) are obtained by a process in which (a) 3-amino-1,2,5-oxadiazoles of the formula (II)

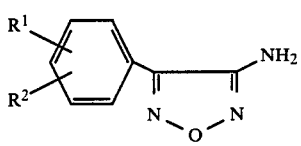

in which
$R^1$ and $R^2$ have the abovementioned meanings, are reacted with iso(thio)cyanates of the formula (III)

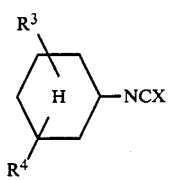

in which
X, $R^3$ and $R^4$ have the abovementioned meanings, if appropriate in the presence of catalysts and if appropriate in the presence of diluents, or (b) 3-iso(thio)cyanato-1,2,5-oxadiazoles of the formula (IV)

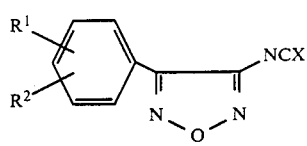

in which
X, $R^1$ and $R^2$ have the abovementioned meanings, are reacted with amines of the formula (V)

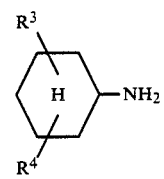

in which
$R^3$ and $R^4$ have the abovementioned meanings, if appropriate in the presence of catalysts and if appropriate in the presence of diluents.

The compounds of the formula (I) can be present in various geometric and optical isomer forms, depending on the arrangement of the substituents bonded to the cyclohexyl radical; they are preferentially obtained in a varying isomer ratio. The present invention relates both to the individual isomers and to the isomer mixtures.

Alkyl $R^1$, $R^2$, $R^3$ and $R^4$ contain in the alkyl part straight-chain or branched alkyl with 1 to 12, preferably 1 to 6 and in particular 1 to 4, carbon atoms. Examples which may be mentioned are methyl, ethyl, n-propyl, i-propyl, n-butyl, i-butyl, sec.-butyl and tert.-butyl.

Alkoxy $R^1$, $R^2$, $R^3$ and $R^4$ contain in the alkyl part straight-chain or branched alkyl with 1 to 12, preferably 1 to 6 and in particular 1 to 4, carbon atoms. Examples which may be mentioned are methoxy, ethoxy, n-propoxy, i-propoxy, n-butoxy, i-butoxy, sec.-butoxy and tert.-butoxy.

Alkylthio $R^1$ and $R^2$ contain in the alkyl part straight-chain or branched alkyl with preferably 1 to 6, in particular 1 to 4, carbon atoms. Examples which may be mentioned are methyl-, ethyl-, n-propyl, i-propyl-, n-butyl-, i-butyl-, sec.-butyl- and tert.-butyl-thio.

Halogenoalkyl and halogenoalkoxy $R^1$, $R^2$, $R^3$ and $R^4$ and halogenoalkylthio $R^1$ and $R^2$ contain in the alkyl part straight-chain or branched alkyl with 1 to 6, preferably 1 to 4 and in particular 1 or 2, carbon atoms and preferably 1 to 6, in particular 1 to 4, halogen atoms, the halogen atoms being identical or different and preferred halogen atoms being fluorine, chlorine or bromine, in particular fluorine.

Examples which may be mentioned are trifluoromethyl, chlorodifluoromethyl, difluoromethyl, trifluoromethylthio, chlorodifluoromethylthio, trifluoroethylthio, chlorotrifluoroethylthio, tetrafluoroethylthio, trifluoromethoxy, difluoromethoxy, tetrafluoroethoxy, chlorotrifluoroethoxy and bromotrifluoroethoxy.

Optionally substituted aryloxy $R^1$ and $R^2$ is aryloxy with 6 to 10 carbon atoms in the aryl part, preferably optionally substituted phenoxy or naphthyloxy, in particular optionally substituted phenoxy.

The optionally substituted aryloxy radicals $R^1$ and $R^2$ can carry one or more, preferably 1 to 3 and in particular 1 or 2, identical or different substituents.

Examples of substituents which may be mentioned are: alkyl with preferably 1 to 4, in particular 1 or 2, carbon atoms, such as methyl, ethyl, n- and i-propyl and n-, i-, sec.- and t-butyl; alkoxy with preferably 1 to 4, in particular 1 or 2, carbon atoms, such as methoxy, ethoxy, n- and i-propoxy and n-, i-, sec.- and t-butoxy; alkylthio with preferably 1 to 4, in particular 1 or 2, carbon atoms, such as methylthio, ethylthio, n- and i-propylthio and n-, i-, sec.- and t-butylthio; halogenoalkyl with preferably 1 to 4, in particular 1 or 2, carbon atoms and preferably 1 to 5, in particular 1 to 3, halogen atoms, the halogen atoms being identical or different and preferred halogen atoms being fluorine, chlorine or bromine, in particular fluorine, such as trifluoromethyl; halogenoalkoxy with preferably 1 to 4, in particular 1 or 2, carbon atoms and preferably 1 to 5, in particular 1 to 3, halogen atoms, the halogen atoms being identical or different and preferred halogen atoms being fluorine, chlorine or bromine, in particular fluorine, such as trifluoromethoxy; halogen, preferably fluorine, chlorine, bromine or iodine, in particular chlorine and bromine; cyano and nitro.

Optionally substituted alkylene, in the definition of $R^1$ and $R^2$, which is interrupted by 1 or 2 oxygen atoms preferably contains 1 to 3, in particular 1 or 2, carbon atoms and can be substituted by $C_1$–$C_4$-alkyl and/or halogen.

Unless described otherwise, halogen represents fluorine, chlorine, bromine or iodine, preferably chlorine or fluorine, it being possible for the halogen atoms to be identical or different.

The radicals $R^1$ and $R^2$ are preferably in the 2-, 4-, 2,4-, 3,4- or 2,6-position of the phenyl ring.

The radicals $R^3$ and $R^4$ are preferably in the 3-, 4-, 3,4- or 3,5-position of the cyclohexyl ring.

The new compounds of the formula (I) have properties which enable them to be used as agents for combating pests, and in particular they are distinguished by an outstanding insecticidal and acaricidal activity.

Preferred new substituted furazanes of the formula (I) are those
in which
$R^1$ and $R^2$ are identical or different and represent hydrogen, halogen, $C_1$–$C_6$-alkyl, $C_1$–$C_6$-alkoxy, $C_1$–$C_6$-alkylthio, halogeno-$C_1$–$C_6$-alkyl, halogeno-$C_1$–$C_6$-alkoxy or halogeno-$C_1$–$C_6$-alkylthio, or represent aryloxy which has 6 to 10 carbon atoms in the aryl part and is optionally substituted by halogen, nitro, cyano, $C_1$–$C_4$-alkyl, $C_1$–$C_4$-alkoxy, $C_1$–$C_4$-alkylthio, halogeno-$C_1$–$C_4$-alkyl, halogeno-$C_1$–$C_4$-alkoxy and/or halogeno-$C_1$–$C_4$-alkylthio, or
$R^1$ and $R^2$ together represent a $C_1$–$C_3$-alkylene radical which is interrupted by 1 or 2 oxygen atoms and is optionally substituted by halogen and/or $C_1$–$C_2$-alkyl,
$R^3$ and $R^4$ are identical or different and represent hydrogen, $C_1$–$C_6$-alkyl, $C_1$–$C_6$-alkoxy, halogeno-$C_1$–$C_6$-alkyl or halogeno-$C_1$–$C_4$-alkoxy and
X represents oxygen or sulphur.

Particularly preferred new substituted furazanes of the formula (I) are those
in which
$R^1$ and $R^2$ are identical or different and represent hydrogen, fluorine, chlorine, bromine, $C_1$–$C_4$-alkyl, $C_1$–$C_4$-alkoxy, $C_1$–$C_4$-alkylthio, halogeno-$C_1$–$C_4$-alkyl, halogeno-$C_1$–$C_4$-alkoxy or halogeno-$C_1$–$C_4$-alkylthio, or represent phenoxy which is optionally substituted by halogen, nitro, cyano, $C_1$–$C_4$-alkyl, $C_1$–$C_4$-alkoxy, $C_1$–$C_4$-alkylthio, halogeno-$C_1$–$C_4$-alkyl, halogeno-$C_1$–$C_4$-alkoxy and/or halogeno-$C_1$–$C_4$-alkylthio, or
$R^1$ and $R^2$ together represent a $C_1$–$C_3$-alkylene radical which is interrupted by 1 or 2 oxygen atoms and is optionally substituted by fluorine, chlorine and/or methyl,
$R^3$ and $R^4$ are identical or different and represent hydrogen, $C_1$–$C_4$-alkyl, $C_1$–$C_4$-alkoxy, halogeno-$C_1$–$C_4$-alkyl or halogeno-$C_1$–$C_4$-alkoxy and
X represents oxygen or sulphur.

Especially preferred new substituted furazanes of the formula (I) are those
in which
$R^1$ and $R^2$ are identical or different and represent hydrogen, fluorine, chlorine, bromine, methoxy, ethoxy, methyl, ethyl, n-propyl, i-propyl, n-butyl, i-butyl, sec.-butyl, tert.-butyl, methylthio, ethylthio, trifluoromethyl, trifluoromethoxy, difluoromethyl, difluoroethyl, pentafluoroethyl, difluoromethoxy, chlorodifluoromethoxy, chlorotrifluoroethoxy, tetrafluoroethoxy, dichlorodifluoroethoxy, difluorotrichloroethoxy, hexafluoropropoxy, trifluoromethylthio, difluoromethylthio, chlorodifluoromethylthio, chlorotrifluoroethylthio or hexafluoropropylthio, or phenoxy which is optionally substituted by fluorine, chlorine, bromine, nitro, cyano, methyl, ethyl, n-propyl, i-propyl, n-butyl, i-butyl, sec.-butyl, tert.-butyl, methoxy, ethoxy, n-propoxy, i-propoxy, n-butoxy, i-butoxy, sec.-butoxy, tert.-butoxy, methylthio, ethylthio, trifluoromethyl, trifluoromethoxy, difluoromethyl, difluoroethyl, pentafluoroethyl, difluoromethoxy, chlorodifluoromethoxy, chlorotrifluoroethoxy, tetrafluoroethoxy, dichlorodifluoroethoxy, difluorotrichloroethoxy, hexafluoropropoxy, trifluoromethylthio, difluoromethylthio, chlorodifluoromethylthio, chlorotrifluoroethylthio and/or hexafluoropropylthio, or
$R^1$ and $R^2$ together represent difluoromethylenedioxy, ethylenedioxy, chlorotrifluoroethylenedioxy, difluoroethylenedioxy, methylenedioxy, trifluoroethylenedioxy, difluoromethyleneoxydifluoromethylenoxy, tetrafluoroethylenedioxy, 2-methyl-1,1,2-trifluoroethylenedioxy or 2,2-dimethylethyleneoxy,
$R^3$ and $R^4$ are identical or different and represent hydrogen, methyl, ethyl, n-propyl, i-propyl, n-butyl, i-butyl, sec.-butyl, tert.-butyl, methoxy, ethoxy, trifluoromethyl, trifluoromethoxy, difluoromethyl, difluoroethyl, pentafluoroethyl, difluoromethoxy, chlorodifluoromethoxy, chlorotrifluoroethoxy, tetrafluoroethoxy, dichlorodifluoroethoxy, difluorotrichloroethoxy or hexafluoropropoxy and
X represents oxygen or sulphur.

Compounds of the formula (I) which are of particular interest are those
in which
$R^1$ and $R^2$ are identical or different and represent hydrogen, fluorine, chlorine, bromine, methyl, methoxy, methylthio, trifluoromethyl, trifluoromethoxy or trifluoromethylthio, or represent phenoxy which is optionally substituted by chlorine, methyl, methoxy, methylthio, trifluoromethyl, trifluoromethoxy and/or trifluoromethylthio, or
$R^1$ and $R^2$ together represent methylenedioxy, ethylenedioxy, difluoromethylenedioxy, tetrafluoroethylenedioxy or chlorotrifluoroethylenedioxy, R[3] and R[4] are identical or different and represent hydrogen, methyl, methoxy, trifluoromethyl or trifluoromethoxy and X represents oxygen or sulphur.

If 3-amino-4-(4-chlorophenyl)-1,2,5-oxadiazole and 3-trifluoromethyl-cyclohexyl isocyanate are used as starting substances according to process variant (a), the course of the reaction can be represented by the following equation:

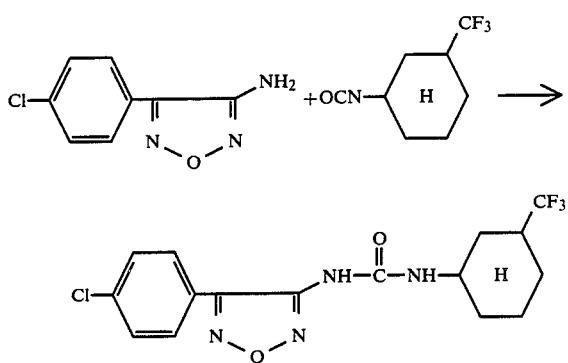

If 4-(4-chlorophenyl)-3-isocyanato-1,2,5-oxadiazole and 4-trifluoromethylcyclohexylamine are used as starting substances according to process variant (b), the course of the reaction can be represented by the following equation:

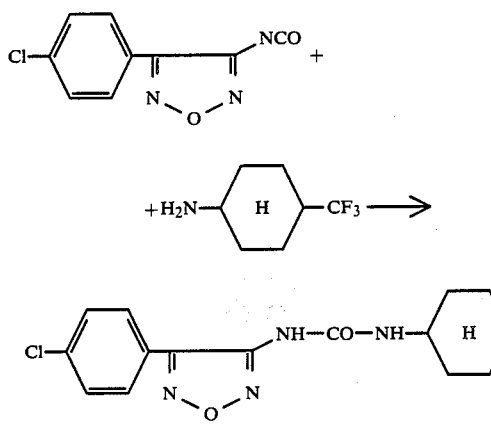

The 3-amino-1,2,5-oxadiazoles of the formula (II) to be used as starting substances are known and/or can be prepared by processes and methods which are known from the literature (compare, J. Prakt. Chem. 315, 4, pages 791-795 (1973)). The amino group can be converted into the isocyanate or isothio-cyanate group by customary processes, for example by reaction with phosgene or thiophosgene in diluents, such as, for example, toluene and/or pyridine, at a temperature between −20° C. and +50° C. (compare the Examples IV-1 to 19 and DE-A-33 26 509).

The compounds of the formulae (III) and (V) are known and/or can be prepared by processes and methods which are known from the literature (compare, for example, DE-OS (German Published Specification) 2,630,562, DE-OS (German Published Specification) 2,528,162 and "Handbuch der organischen Chemie" ("Handbook of Organic Chemistry"), Volume 12 and supplementary volumes, Beilstein).

Possible diluents in the process (variants (a) and (b)) according to the invention are virtually all the inert organic solvents. These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylacetamide and N-methyl-pyrrolidone, and tetramethylene sulphone and dimethylformamide.

Catalysts which can be used for the reaction according to process variants (a) and (b) are preferably tertiary amines, such as triethylamine and 1,4-diazabicyclo[2,2,-2]octane, and organic tin compounds, such as, for example, dibutyl-tin dilaurate.

The reaction temperature can be varied within a substantial range. In general, the reaction is carried out between 20° C. and 180° C., preferably between 40° C. and 120° C., in process variant (a) and between 20° C. and 200° C., preferably between 60° C. and 190° C., in process variant (b). The process variants according to the invention are in general carried out under normal pressure.

For carrying out the process variants according to the invention, the starting substances are usually employed in approximately equimolar amounts. An excess of one or the other of the reaction components provides no substantial advantages.

The reaction products are worked up by customary methods, for example by a procedure in which the product which has precipitated is filtered off with suction or undesirable by-products are dissolved out of the reaction mixture. The products are characterized by their melting points.

The active compounds are well tolerated by plants, have a favorable level of toxicity to warm-blooded animals, and are suitable for combating animal pests, especially insects and arachnida, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and *Scutigera spec.* From the order of the Symphyla, for example, *Scutigerella immaculata.* From the order of the Thysanura, for example, *Lepisma saccharina.* From the order of the Collembola, for example, *Onychiurus armatus.* From the order of Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,*

Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homonoa magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestris,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as can extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as naturally occurring phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms and the like.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The biological activity of the compounds according to the invention may be illustrated with the aid of the following examples.

EXAMPLE A

Development inhibition test with *Tetranychus urticae* (common spider mite)

Solvent: 3 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

The leaves of bean plants (*Phaseolus vulgaris*) on which about 100 eggs of the common spider mite have been deposited are immersed in the active compound preparation of appropriate concentration. The total of destroyed eggs, larvae, nymphs and chrysalis stages of a generation, based on the number of eggs used, gives the destruction in %. 100% means that all of the mites have been destroyed; 0% means that none of the mites have been destroyed.

In this test, for example, the compounds of preparation Examples (3), (12) and (28), show a destruction of 90 to 100% at an active compound concentration of 0.0008%.

EXAMPLE B

Tetranychus test (systemic effect)

Solvent: 3 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) are watered with in each cse 50 ml of the preparation of the active compound of the desired concentration so that the active compound preparation penetrates into the soil without wetting the plant. The active compound is taken up by the roots and passed to the shoot.

After one day, spider mites (*Tetranychus urticae*) are allowed to deposit eggs on the leaves, and the adult spider mites are removed. The destruction of the development stages in % is determined. 100% means that all the spider mites have been killed; 0% means that none of the spider mites have been killed.

In this test, for example, the compounds of preparation Examples (2), (3), (7), (12) and (28) show a destruction of 100% at an active compound concentration of 0.1%.

The preparation of the compounds according to the invention may be illustrated by the following preparation examples:

EXAMPLE 1

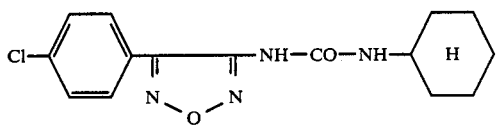

(Process variant a)

7.84 g (0.04 mole) of 3-amino-4-(4-chlorophenyl)-1,2,5-oxadiazole are dissolved in 28 ml of dry dimethylformamide. 7 g (0.028 mole) of cyclohexyl isocyanate are added to the solution. The mixture is stirred at 100° C. for 10 hours. On cooling to 20° C., the product precipitates. It is filtered off with suction and covered with a little dimethylformamide. The mixture is then covered with toluene and subsequently with petroleum ether and the product is dried.

9 g (70.3% of theory) of 1-[4-(4-chlorophenyl)-1,2,5-oxadiazol-3-yl]-3-cyclohexylurea of melting point 216° C. are obtained.

EXAMPLE 2

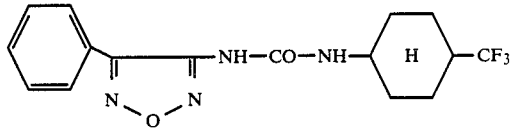

(Process variant b)

37.4 g (0.2 mole) of 3-isocyanato-4-phenyl-1,2,5-oxadiazole, dissolved in 200 ml of dry toluene, are added to a solution of 33.2 g (0.2 mole) of 4-trifluoromethylcyclohexylamine in 800 ml of dry toluene with exclusion of moisture. The mixture is stirred at 80° C. for half an hour and most of the solvent is then distilled off in vacuo. The crystalline residue is filtered off with suction and washed with petroleum ether.

65.6 g (92.5% of theory) of 1-(4-phenyl-1,2,5-oxadiazol-3-yl)-3-(4-trifluoromethylcyclohexyl)-urea of melting point 212° C. are obtained.

The compounds of the formula (I) listed in the following Table 1 are prepared analogously to Example 1 and 2 or process variant (a) or (b):

TABLE 1

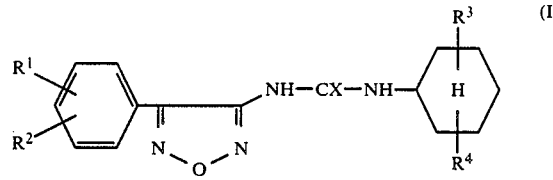
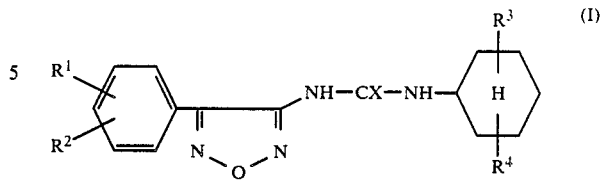

(I)

| Example No. | R¹ | R² | R³ | R⁴ | X | Melting point [°C.] |
|---|---|---|---|---|---|---|
| 3 | 4-Cl | H | 4-CF₃ | H | O | 203 |
| 4 | 4-Cl | H | 3-CF₃ | H | O | 190 |
| 5 | 4-Cl | H | 3-CF₃ | 5-CF₃ | O | 189 |
| 6 | H | H | 3-CF₃ | 5-CF₃ | O | 200 |
| 7 | H | H | 3-CF₃ | H | O | 171 |
| 8 | H | H | H | H | O | 196 |
| 9 | H | H | H | 4-CH₃ | O | 213 |
| 10 | H | H | H | 2-CH₃ | O | 198 |
| 11 | H | H | H | 3-CH₃ | O | 176 |
| 12 | 2-Cl | H | H | 4-CF₃ | O | 223 |
| 13 | 2-Cl | H | H | 3-CF₃ | O | 219 |
| 14 | 2-Cl | H | H | H | O | 212 |
| 15 | 2-Cl | H | H | 4-CH₃ | O | 206 |
| 16 | 4-Cl | H | H | 2-CF₃ | O | 208 |
| 17 | H | H | H | 2-CF₃ | O | 219 |
| 18 | 2-Cl | 4-Cl | H | 3-CF₃ | O | 193 |
| 19 | 2-Cl | 4-Cl | H | 4-CF₃ | O | 199 |
| 20 | 2-Cl | 4-Cl | 3-CF₃ | 5-CF₃ | O | 231 |
| 21 | 2-Cl | 4-Cl | H | 4-CH₃ | O | 186 |
| 22 | 2-Cl | 4-Cl | H | 2-CH₃ | O | 210 |
| 23 | 4-F | H | H | 4-CF₃ | O | 196 |
| 24 | 4-F | H | H | 3-CF₃ | O | 158 |
| 25 | 4-F | H | H | 4-CH₃ | O | 180 |
| 26 | 4-F | H | 3-CF₃ | 5-CF₃ | O | 198 |
| 27 | 4-Br | H | H | 4-CH₃ | O | 205 |
| 28 | 4-Br | H | H | 4-CF₃ | O | 200 |
| 29 | 4-F | H | H | H | O | 197 |
| 30 | 4-Br | H | H | 3-CF₃ | O | 207 |
| 31 | 4-Br | H | 3-CF₃ | 5-CF₃ | O | 190 |
| 32 | 4-CF₃ | H | H | 4-CF₃ | O | 156 |
| 33 | 4-CF₃ | H | H | 3-CF₃ | O | 200 |
| 34 | 4-CF₃ | H | 3-CF₃ | 5-CF₃ | O | 182 |
| 35 | 4-CF₃ | H | H | 3-CH₃ | O | 197 |
| 36 | 4-CF₃O | H | H | 4-CF₃ | O | 174 |
| 37 | 4-CF₃–⌬–O– | H | H | 4-CF₃ | O | 194 |
| 38 | 4-CH₃O | H | H | 4-CF₃ | O | 212 |
| 39 | 4-CH₃O | H | H | 4-CH₃ | O | 170 |
| 40 | 4-CH₃O | H | H | 3-CF₃ | O | 193–196 |
| 41 | 4-CH₃ | H | 3-CF₃ | 5-CF₃ | O | 201 |
| 42 | 4-CH₃ | H | H | 4-CF₃ | O | 203 |
| 43 | 3,4-O—CH₂—O— | | H | 4-CF₃ | O | 206 |
| 44 | 4-CH₃ | H | H | 4-CH₃ | O | 197 |
| 45 | 4-CF₃–⌬–O– | H | H | 3-CF₃ | O | 173 |
| 46 | 4-CH₃ | H | H | 3-CF₃ | O | 191 |
| 47 | 3,4-O—CH₂—O— | | H | H | O | 227 |
| 48 | 3,4-O—CH₂—O— | | H | 4-CH₃ | O | 205 |
| 49 | 3,4-O—CH₂—O— | | H | 3-CF₃ | O | 205 |
| 50 | 3-Cl | 4-Cl | H | 4-CF₃ | O | 186 |
| 51 | 3-Cl | 4-Cl | H | 3-CF₃ | O | 206 |
| 52 | 3-Cl | 4-Cl | H | 4-CH₃ | O | 175 |
| 53 | 4-CF₃S | H | H | 4-CF₃ | O | 187 |
| 54 | 4-CF₃–⌬(2-Cl)–O– | H | H | 4-CF₃ | O | 187 |
| 55 | 4-CF₃–⌬(2,6-Cl₂)–O– | H | H | 4-CF₃ | O | 182 |
| 56 | H | H | 3-CF₃ | 4-CH₃O | O | 186 |
| 57 | H | H | 2-CH₃O | 5-CF₃ | O | 225 |
| 58 | 4-Cl | H | 3-CF₃ | 4-CH₃O | O | 124 |
| 59 | 4-Cl | H | 2-CH₃O | 5-CF₃ | O | 219 |
| 60 | 4-F | H | 3-CF₃ | 4-CH₃O | O | 187 |
| 61 | 4-Br | H | 2-CH₃O | 5-CF₃ | O | 220 |
| 62 | 2-Cl | 4-Cl | 3-CF₃ | 4-CH₃O | O | 179 |
| 63 | 4-CF₃ | H | 3-CF₃ | 4-CH₃O | O | 160 |
| 64 | 4-CF₃O | H | 3-CF₃ | 4-CH₃O | O | 163 |
| 65 | 4-CF₃–⌬–O– | H | 3-CF₃ | 4-CH₃O | O | 186 |
| 66 | 4-CF₃–⌬–O– | H | 2-CH₃O | 5-CF₃ | O | 162 |
| 67 | H | H | H | 4-CF₃ | S | 159 |
| 68 | H | H | 3-CF₃ | 5-CF₃ | S | 128 |
| 69 | H | H | H | 3-CF₃ | S | 142 |
| 70 | 3–⌬–O– | H | H | 4-CF₃ | O | 209 |
| 71 | 3–⌬–O– | 4-F | H | 4-CF₃ | O | 215 |
| 72 | 2-Cl | H | H | 4-CF₃ | S | 150 |
| 73 | 2-Cl | H | 3-CF₃ | 5-CF₃ | S | 150 |
| 74 | H | H | 2-CH₃O | 5-CF₃ | S | 169 |
| 75 | H | H | 3-CF₃ | 4-CH₃O | S | 152 |
| 76 | 3–⌬–O– | 4-F | 3-CF₃ | 4-CH₃O | O | 150 |
| 77 | 2-Cl | H | 2-CH₃O | 5-CF₃ | O | 242 |
| 78 | 2-Cl | H | 2-CH₃O | 5-CF₃ | S | 179 |
| 79 | 2-Cl | H | 3-CF₃ | 4-CH₃O | O | 221 |
| 80 | 2-Cl | H | 3-CF₃ | 4-CH₃O | S | 152 |
| 81 | 4-F | H | 3-CF₃ | 6-CH₃O | O | 195 |
| 82 | H | H | 3-CF₃ | 4-CH₃ | O | 170 |
| 83 | 4-Cl | H | 3-CF₃ | 4-CH₃ | O | 165 |
| 84 | 2-Cl | H | 3-CF₃ | 4-CH₃ | O | 203 |
| 85 | 4-Br | H | 3-CF₃ | 4-CH₃ | O | 164 |
| 86 | H | H | 2-CF₃ | 4-CF₃ | O | 226 |
| 87 | 4-Cl | H | 2-CF₃ | 4-CF₃ | O | 186 |
| 88 | 2-Cl | H | 2-CF₃ | 4-CF₃ | O | 227 |
| 89 | 4-Br | H | 2-CF₃ | 4-CF₃ | O | 192 |
| 90 | H | H | 3-CF₃ | 4-CH₃ | S | 144 |
| 91 | 2-Cl | H | 3-CF₃ | 4-CH₃ | S | 139 |
| 92 | H | H | 2-CF₃ | 4-CF₃ | S | 110 |
| 93 | 2-Cl | H | 2-CF₃ | 4-CF₃ | S | 115 |
| 94 | 4-F | H | 2-CF₃ | 4-CF₃ | O | 220 |
| 95 | 4-F | H | 3-CF₃ | 4-CH₃ | O | 171 |

TABLE 1-continued (I)

R¹–[phenyl with R²]–C(=N-O-N=)–NH–CX–NH–[cyclohexyl with R³, R⁴, H]

| Example No. | R¹ | R² | R³ | R⁴ | X | Melting point [°C.] |
|---|---|---|---|---|---|---|
| 96 | 4-F₃C—⟨phenyl⟩—O— | H | 2-CF₃ | 4-CF₃ | O | 161 |
| 97 | 2-Cl | 4-Cl | 2-CF₃ | 4-CF₃ | O | 196 |
| 98 | 4-CF₃ | H | 2-CF₃ | 4-CF₃ | O | 160 |
| 90 | 2-Cl | 4-Cl | 3-CF₃ | 4-CH₃ | O | 195 |
| 100 | 4-CF₃ | H | 3-CF₃ | 4-CH₃ | O | 142 |
| 101 | 4-OCF₃ | H | 2-CF₃ | 4-CF₃ | O | 176 |
| 102 | 4-OCH₃ | H | 2-CF₃ | 4-CF₃ | O | 152 |
| 103 | 4-OCF₃ | H | 3-CF₃ | 4-CH₃ | O | 130 |
| 104 | 4-OCH₃ | H | 3-CF₃ | 4-CH₃ | O | 184 |
| 105 | 4-F₃C—⟨phenyl⟩—O— | H | 3-CF₃ | 4-CH₃ | O | 105 (decomposition) |

Starting substance of the formula (IV)

Example (IV-1)

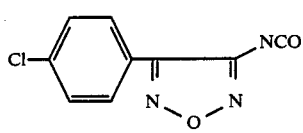

400 ml of dry toluene are gassed with 50 g of phosgene at 0° C. to 5° C. A solution of 58.7 g (0.3 mole) of 3-amino-4-(4-chlorophenyl)-1,2,5-oxadiazole and 52.2 g (0.66 mole) of pyridine in 400 ml of toluene is added dropwise to this cold solution at −10° C. to +5° C. and the mixture is stirred at 30° C. for 2 hours. The salts which have precipitated are filtered off with suction, with exclusion of moisture, the filtrate is concentrated and the residue is distilled in vacuo.

30.5 g (54.5% of theory) of 4-(4-chlorophenyl)-3-isocyanato-1,2,5-oxadiazole of boiling point b.p.₂: 108° C. to 112° C. are obtained.

The remaining compounds of the formula (IV) can be obtained analogously to Example (IV-1):

TABLE 2

(IV)

| Example No. | R¹ | R² | X | Physical constants |
|---|---|---|---|---|
| IV-2 | H | H | O | Mp: 53–54° C. |
| IV-3 | H | 2-Cl | O | $n_D^{20}$: 1 5646 |
| IV-4 | 2-Cl | H | S | $n_D^{20}$: 1 6242 |
| IV-5 | 4-F | H | O | Mp: 80° C. |
| IV-6 | 4-Br | H | O | Mp: 82° C. |

TABLE 2-continued (IV)

| Example No. | R¹ | R² | X | Physical constants |
|---|---|---|---|---|
| IV-7 | 4-CF₃ | H | O | $n_D^{20}$: 1 5079 |
| IV-8 | 4-CF₃O | H | O | $n_D^{20}$: 1 4986 |
| IV-9 | 4-CH₃O | H | O | Mp: 42° C. |
| IV-10 | 4-CH₃ | H | O | Mp: 52° C. |
| IV-11 | 4-CF₃S | H | O | $n_D^{20}$: 1 5378 |
| IV-12 | 2-Cl | 4-Cl | O | Mp: 67° C. |
| IV-13 | 3-Cl | 4-Cl | O | Mp: 40° C. |
| IV-14 | 4-CF₃—⟨phenyl⟩—O— | H | O | $n_D^{20}$: 1 5585 |
| IV-15 | 4-CF₃—⟨phenyl-Cl⟩—O— | H | O | $n_D^{20}$: 1 5663 |
| IV-16 | 4-CF₃—⟨phenyl-Cl,Cl⟩—O— | H | O | Mp: 70° C. |
| IV-17 | 3-⟨phenyl⟩—O— | H | O | $n_D^{20}$: 1 5988 |
| IV-18 | 4-F | 3-⟨phenyl⟩—O— | O | $n_D^{20}$: 1 5860 |
| IV-19 | H | H | S | $n_D^{20}$: 1 6298 |

It is understood that the specification and examples are illustrative but not limitative of the present invention and that other embodiments within the spirit and scope of the invention will suggest themselves to those skilled in the art.

We claim:

1. A substituted furazane of the formula

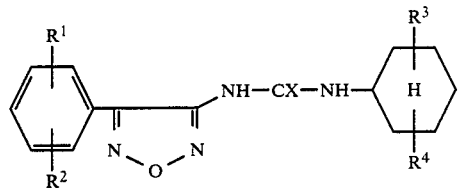

in which

R¹ and R² each independently is hydrogen, halogen, C₁–C₆-alkyl, C₁–C₆-alkoxy, C₁–C₆-alkylthio, halogeno-C₁–C₆-alkyl, halogeno-C₁–C₆-alkoxy or halogeno-C₁–C₆-alkylthio, or is aryloxy which has 6 to 10 carbon atoms in the aryl part and is optionally substituted by halogen, nitro, cyano, C₁–C₄-alkyl, C₁–C₄-alkoxy, C₁–C₄-alkylthio, halogeno-C₁–C₄-alkyl, halogeno-C₁–C₄-alkoxy and/or halogeno-C₁–C₄-alkylthio, or R¹ and R² together are a C₁–C₃-alkylene radical which is interrupted by 1 or 2 oxygen atoms and is optionally substituted by halogen and/or $C_1-C_2$-alkyl, and $R^3$ and $R^4$ each independently is hydrogen, $C_1-C_6$-alkyl, $C_1-C_6$-alkoxy, halogeno-$C_1-C_6$-alkyl or halogeno $C_1-C_4$-alkoxy, and X is oxygen or sulphur.

2. A compound according to claim 1, in which $R^1$ and $R^2$ each independently is hydrogen, fluorine, chlorine, bromine, $C_1-C_4$-alkyl, $C_1-C_4$-alkoxy, $C_1-C_4$-alkylthio, halogeno-$C_1-C_4$-alkyl, halogeno-$C_1-C_4$-alkoxy, halogeno-$C_1-C_4$-alkylthio, or phenoxy which is optionally substituted by halogen, nitro, cyano, $C_1-C_4$-alkyl, $C_1-C_4$-alkoxy, $C_1-C_4$-alkylthio, halogeno-$C_1-C_4$-alkyl, halogeno-$C_1-C_4$-alkoxy and/or halogeno-$C_1-C_4$-alkylthio, or $R^1$ and $R^2$ together are a $C_1-C_3$-alkylene radical which is interrupted by 1 or 2 oxygen atoms and is optionally substituted by fluorine, chlorine and/or methyl, and $R^3$ and $R^4$ are identical or different and represent hydrogen, $C_1-C_4$-alkyl, $C_1-C_4$-alkoxy, halogeno-$C_1-C_4$-alkyl or halogeno-$C_1-C_4$-alkoxy.

3. A compound according to claim 1, in which $R^1$ and $R^2$ each independently is hydrogen, fluorine, chlorine, bromine, methyl, methoxy, methylthio, trifluoromethyl, trifluoromethoxy, trifluoromethylthio, or phenoxy which is optionally substituted by chlorine, methyl, methoxy, methylthio, trifluoromethyl, trifluoromethoxy and/or trifluoromethylthio, or $R^1$ and $R^2$ together are methylenedioxy, ethylenedioxy, difluoromethylenedioxy, tetrafluoroethylenedioxy or chlorotrifluoroethylenedioxy, and $R^3$ and $R^4$ each independently is hydrogen, methyl, methoxy, trifluoromethyl or trifluoromethoxy.

4. A compound according to claim 1, wherein such compound is 1-(4-phenyl-1,2,5-oxadiazol-3-yl)-3-(4-trifluoromethylcyclohexyl)-urea of the formula

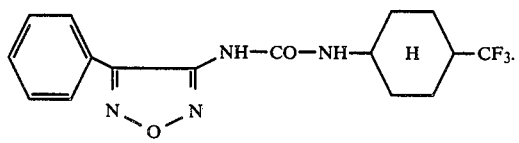

5. A compound according to claim 1, wherein such compound is 1-[4-(4-chlorophenyl)-1,2,5-oxadiazol-3-yl]-3-(4-trifluoromethylcyclohexyl)-urea of the formula

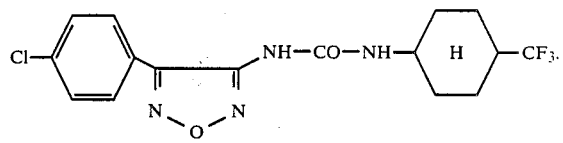

6. A compound according to claim 1, wherein such compound is 1-[4-(4-chlorophenyl)-1,2,5-oxadiazol-3-yl]-3-(3-trifluoromethylcyclohexyl)-urea of the formula

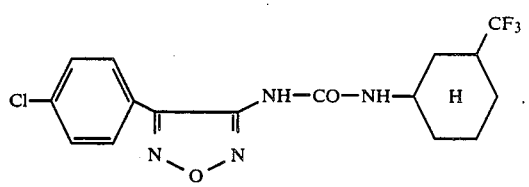

7. A compound according to claim 1, wherein such compound is 1-[4-(2-chlorophenyl)-1,2,5-oxadiazol-3-yl]-3-(4-trifluoromethylcyclohexyl-urea of the formula

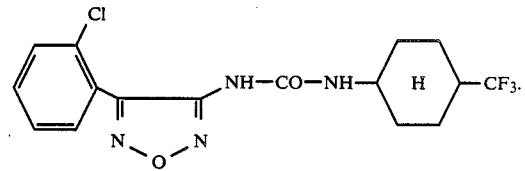

8. A compound according to claim 1, wherein such compound is 1-[4-(4-bromophenyl)-1,2,5-oxadiazol-3-yl]-3-(4-trifluoromethylcyclohexyl)-urea of the formula

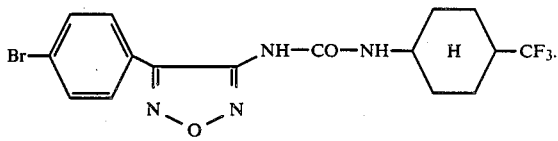

9. An insecticidal or acaricidal composition comprising an insecticidally or acaricidally effective amount of a compound according to claim 1 in admixture with a diluent.

10. A method of combating insects or acarids which comprises applying thereto or to a habitat thereof an insecticidally or acaricidally effective amount of a compound according to claim 1.

11. The method according to claim 10, wherein such compound is
1-(4-phenyl-1,2,5-oxadiazol-3-yl)-3-(4-trifluoromethylcyclohexyl)-urea,
1-[4-(4-chlorophenyl)-1,2,5-oxadiazol-3-yl]-3-(4-trifluoromethylcyclohexyl)-urea,
1-[4-(4-chlorophenyl)-1,2,5-oxadiazol-3-yl-3-(3-trifluoromethylcyclohexyl)-urea,
1-[4-(2-chlorophenyl)-1,2,5-oxadiazol-3-yl]-3-(4-trifluoromethylcyclohexyl-urea or
1-[4-(4,bromophenyl)-1,2,5-oxadiazol-3-yl]-3-(4-trifluoromethylcyclohexyl)-urea.

* * * * *